United States Patent
Li et al.

(10) Patent No.: US 9,949,648 B2
(45) Date of Patent: *Apr. 24, 2018

(54) CONTINUOUS NON-INVASIVE BLOOD PRESSURE MEASUREMENT APPARATUS AND METHODS PROVIDING AUTOMATIC RECALIBRATION

(71) Applicant: Nellcor Puritan Bennett Ireland, Mervue, Galway (IE)

(72) Inventors: Luya Li, Coquitlam (CA); Rakesh Kumar Sethi, Vancouver (CA); Ming Sun, New Westminster (CA); Alexander Yuk Sit, Richmond (CA); Yong Liu, Vancouver (CA)

(73) Assignee: Nellcor Puritan Bennett Ireland, Galway (IE)

( * ) Notice: Subject to any disclaimer, the term of this patent is extended or adjusted under 35 U.S.C. 154(b) by 958 days.

This patent is subject to a terminal disclaimer.

(21) Appl. No.: 14/022,090

(22) Filed: Sep. 9, 2013

(65) Prior Publication Data

US 2014/0012147 A1    Jan. 9, 2014

Related U.S. Application Data

(63) Continuation of application No. 12/275,453, filed on Nov. 21, 2008, now Pat. No. 8,560,245, which is a (Continued)

(51) Int. Cl.
*A61B 5/022* (2006.01)
*A61B 5/021* (2006.01)
(Continued)

(52) U.S. Cl.
CPC .............. *A61B 5/022* (2013.01); *A61B 5/021* (2013.01); *A61B 5/02116* (2013.01);
(Continued)

(58) Field of Classification Search
None
See application file for complete search history.

(56) References Cited

U.S. PATENT DOCUMENTS 3,835,840 A    9/1974 Mount
4,561,447 A    12/1985 Kawamura et al.
(Continued)

FOREIGN PATENT DOCUMENTS

EP    0443267    8/1991
EP    0755221    1/1997
(Continued)

OTHER PUBLICATIONS

Fung, YC, Biomechanics: Circulation, 2nd Edition, New York, Springer, 1997, pp. 1-571.
(Continued)

*Primary Examiner* — Larry D Riggs, II

(57) ABSTRACT

A blood pressure measurement system is configured to perform a calibration automatically when a calibration condition is satisfied. The calibration condition is based upon one or more parameters of pulse waves of a subject. The parameters may include pulse wave area; a time difference between systolic peak and reflected wave peak or dichrotic notch in the pulse wave and a shape of at least a portion of the pulse wave.

17 Claims, 3 Drawing Sheets

Related U.S. Application Data continuation of application No. 11/015,033, filed on Dec. 20, 2004, now Pat. No. 7,455,643, which is a continuation-in-part of application No. 10/884,962, filed on Jul. 7, 2004, now abandoned.

(60) Provisional application No. 60/484,640, filed on Jul. 7, 2003.

(51) Int. Cl.
*A61B 5/0225* (2006.01)
*A61B 5/00* (2006.01)

(52) U.S. Cl.
CPC ........ *A61B 5/02125* (2013.01); *A61B 5/0225* (2013.01); *A61B 5/7239* (2013.01)

(56) References Cited

U.S. PATENT DOCUMENTS

| | | | |
|---|---|---|---|
| 4,592,365 A | 6/1986 | Georgi | |
| 4,676,253 A | 6/1987 | Newman | |
| 4,718,428 A | 1/1988 | Russell | |
| 4,729,382 A | 3/1988 | Schaffer | |
| 4,830,017 A | 5/1989 | Perry | |
| 4,836,213 A | 6/1989 | Wenzel et al. | |
| 4,854,327 A | 8/1989 | Kunig | |
| 4,870,973 A | 10/1989 | Ueno | |
| 4,898,176 A | 2/1990 | Petre | |
| 4,924,871 A | 5/1990 | Honeyager | |
| 4,928,700 A | 5/1990 | Harada | |
| 4,951,679 A | 8/1990 | Harada | |
| 4,976,268 A | 12/1990 | Kurosawa et al. | |
| 4,987,900 A | 1/1991 | Eckerle | |
| 5,065,765 A | 11/1991 | Eckerle | |
| 5,103,831 A | 4/1992 | Niwa | |
| 5,105,815 A | 4/1992 | Hall et al. | |
| 5,111,817 A | 5/1992 | Clark et al. | |
| 5,119,824 A | 6/1992 | Niwa | |
| 5,131,400 A | 7/1992 | Harada | |
| 5,163,328 A | 11/1992 | Holland | |
| 5,165,416 A | 11/1992 | Shinoda | |
| 5,170,796 A | 12/1992 | Kobayashi | |
| 5,176,143 A | 1/1993 | Eckerle et al. | |
| 5,178,154 A | 1/1993 | Ackmann et al. | |
| 5,179,956 A | 1/1993 | Harada et al. | |
| 5,204,922 A | 4/1993 | Weir | |
| 5,238,000 A | 8/1993 | Niwa | |
| 5,241,964 A | 9/1993 | McQuilkin | |
| 5,247,931 A | 9/1993 | Norwood | |
| 5,255,686 A | 10/1993 | Takeda et al. | |
| D340,990 S | 11/1993 | Kawamura | |
| 5,269,312 A | 12/1993 | Kawamura et al. | |
| 5,289,823 A | 3/1994 | Eckerle | |
| 5,309,917 A | 5/1994 | Wang | |
| 5,379,774 A | 1/1995 | Nishimura et al. | |
| 5,431,159 A | 7/1995 | Baker | |
| 5,450,852 A | 9/1995 | Archibald et al. | |
| 5,467,771 A | 11/1995 | Narimatsu | |
| 5,485,838 A | 1/1996 | Ukawa et al. | |
| 5,490,506 A | 2/1996 | Takatani | |
| 5,494,043 A | 2/1996 | O'Sullivan et al. | |
| 5,497,779 A | 3/1996 | Takaya | |
| 5,505,209 A | 4/1996 | Reining | |
| 5,533,511 A * | 7/1996 | Kaspari | A61B 5/02007 128/925 |
| 5,535,753 A | 7/1996 | Petrucelli et al. | |
| 5,562,621 A | 10/1996 | Claude et al. | |
| 5,564,427 A | 10/1996 | Aso et al. | |
| 5,575,284 A | 11/1996 | Athan | |
| 5,590,649 A | 1/1997 | Caro et al. | |
| 5,617,868 A | 4/1997 | Harada | |
| 5,640,964 A | 6/1997 | Archibald et al. | |
| 5,649,542 A | 7/1997 | Archibald et al. | |
| 5,649,543 A | 7/1997 | Hosaka et al. | |
| 5,676,139 A | 10/1997 | Goldberger et al. | |
| 5,676,140 A | 10/1997 | Ukawa | |
| 5,682,898 A | 11/1997 | Aung | |
| 5,685,316 A | 11/1997 | Schookin et al. | |
| 5,697,371 A | 12/1997 | Aoyagi et al. | |
| 5,704,362 A | 1/1998 | Hersh et al. | |
| 5,709,212 A | 1/1998 | Sugo | |
| 5,720,292 A | 2/1998 | Poliac | |
| 5,722,414 A | 3/1998 | Archibald et al. | |
| 5,738,103 A | 4/1998 | Poliac | |
| 5,743,856 A | 4/1998 | Oka et al. | |
| 5,755,669 A | 5/1998 | Ono et al. | |
| 5,762,610 A | 6/1998 | Narimatsu | |
| 5,772,601 A | 6/1998 | Oka | |
| 5,772,602 A | 6/1998 | Sakai | |
| 5,776,071 A | 7/1998 | Inukai | |
| 5,785,659 A | 7/1998 | Caro et al. | |
| 5,791,347 A | 8/1998 | Flaherty et al. | |
| 5,797,395 A | 8/1998 | Martin | |
| 5,797,850 A | 8/1998 | Archibald et al. | |
| 5,810,734 A | 9/1998 | Caro et al. | |
| 5,810,736 A | 9/1998 | Pail | |
| 5,827,181 A | 10/1998 | Dias | |
| 5,830,131 A | 11/1998 | Caro et al. | |
| 5,832,924 A | 11/1998 | Archibald et al. | |
| 5,833,618 A | 11/1998 | Caro | |
| 5,848,970 A | 12/1998 | Voss | |
| 5,857,975 A | 1/1999 | Golub | |
| 5,865,755 A | 2/1999 | Golub | |
| 5,873,834 A | 2/1999 | Yanagi et al. | |
| 5,904,654 A | 5/1999 | Wohltmann et al. | |
| 5,938,618 A | 8/1999 | Archibald et al. | |
| 5,941,828 A | 8/1999 | Archibald et al. | |
| 5,964,711 A | 10/1999 | Voss | |
| 5,993,394 A | 11/1999 | Poliac | |
| 6,002,952 A | 12/1999 | Diab | |
| 6,004,274 A | 12/1999 | Nolan | |
| 6,007,492 A | 12/1999 | Goto et al. | |
| 6,011,986 A | 1/2000 | Diab et al. | |
| 6,017,314 A | 1/2000 | Poliac | |
| 6,022,320 A | 2/2000 | Ogura | |
| 6,027,452 A | 2/2000 | Flaherty et al. | |
| 6,027,453 A | 2/2000 | Miwa | |
| 6,027,455 A | 2/2000 | Inukai et al. | |
| 6,045,509 A | 4/2000 | Caro et al. | |
| 6,067,462 A | 5/2000 | Diab | |
| 6,083,171 A | 7/2000 | Ono et al. | |
| 6,095,987 A | 8/2000 | Shmulewitz | |
| 6,099,477 A | 8/2000 | Archibald et al. | |
| 6,132,382 A | 10/2000 | Archibald et al. | |
| 6,135,966 A | 10/2000 | Ko | |
| 6,157,850 A | 12/2000 | Diab et al. | |
| 6,159,157 A | 12/2000 | Archibald et al. | |
| 6,161,038 A | 12/2000 | Schookin et al. | |
| 6,176,831 B1 | 1/2001 | Voss et al. | |
| 6,186,954 B1 | 2/2001 | Narimatsu | |
| 6,186,955 B1 | 2/2001 | Baura | |
| 6,190,325 B1 | 2/2001 | Narimatsu | |
| 6,190,382 B1 | 2/2001 | Ormsby et al. | |
| 6,196,974 B1 | 3/2001 | Miwa | |
| 6,217,524 B1 | 4/2001 | Orr et al. | |
| 6,227,196 B1 | 5/2001 | Jaffe et al. | |
| 6,228,034 B1 | 5/2001 | Voss et al. | |
| 6,241,661 B1 | 6/2001 | Schluess et al. | |
| 6,241,679 B1 | 6/2001 | Curran | |
| 6,245,022 B1 | 6/2001 | Archibald et al. | |
| 6,251,081 B1 | 6/2001 | Narimatsu | |
| 6,263,222 B1 | 7/2001 | Diab et al. | |
| 6,292,689 B1 | 9/2001 | Wallace | |
| 6,293,915 B1 | 9/2001 | Amano et al. | |
| 6,299,582 B1 | 10/2001 | Brockway et al. | |
| 6,332,867 B1 | 12/2001 | Chen et al. | |
| 6,340,349 B1 | 1/2002 | Archibald et al. | |
| 6,350,242 B1 | 2/2002 | Doten et al. | |
| 6,371,921 B1 | 4/2002 | Caro | |
| D458,375 S | 6/2002 | Thede | |
| 6,443,905 B1 | 9/2002 | Nissila et al. | |
| 6,463,311 B1 | 10/2002 | Diab | |
| 6,470,893 B1 | 10/2002 | Boesen | |
| 6,471,646 B1 | 10/2002 | Thede | |

(56) References Cited

U.S. PATENT DOCUMENTS

| | | |
|---|---|---|
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,577,892 B2 | 6/2003 | Schomburg |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 2002/0058876 A1* | 5/2002 | Chen ............... A61B 5/021 600/485 |
| 2002/0095090 A1 | 7/2002 | Caro et al. |
| 2003/0036690 A1 | 2/2003 | Geddes et al. |
| 2003/0135124 A1 | 7/2003 | Russell et al. |
| 2005/0148885 A1 | 7/2005 | Tweed et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0249467 A1 | 10/2007 | Hong et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0132798 A1 | 6/2008 | Hong et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2009/0048497 A1 | 2/2009 | Keren |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |
| WO | WO 9611625 | 4/1996 |
| WO | WO 9714355 | 4/1997 |
| WO | WO 9714356 | 4/1997 |
| WO | WO 9712543 | 10/1997 |
| WO | WO 9712565 | 10/1997 |
| WO | WO 9806327 | 2/1998 |
| WO | WO 9825516 | 6/1998 |

OTHER PUBLICATIONS

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb., 1991, pp. 39-54.

Nara, Andrew R., Burns, Michael P., Downs, W. Gregory, Blood Pressure, Redmond, Washington, SpaceLabs, 1989, pp. 1-109.

Geddes, LA, Handbook of Blood Pressure Measurement, Clifton, New Jersey, Humana Press, 1991, pp. 1-168.

Moyle, John TB, Hahn, Cew, Adams, Anthony P, Pulse Oximetry, Revised Edition, London, BMJ, 1998, pp. 1-140.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990, pp. 1-456.

Berne, Robert M., Levy, Matthew N., eds., Physiology, 2nd edition, St. Louis, Mosby, 1988, pp. 357-681.

Young, Christopher C., Mark, Jonathan B., White, William, Debree, Ashley, Vender, Jefferys., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Fletcher, Gerald F., ed., Cardiovascular Response to Exercise, Mt. Kisco, NY, Futura Publishing Co., 1994, pp. 1-446.

Woodcock, John P, Theory and Practice of Blood Flow Measurement, London, Butterworths & Co, 1975, pp. 1-274.

Greenfield, ADM, Shepherd, JT, "A Quantitative Study of the Response to Cold of the Circulation through the Fingers of Normal Subjects," Clinical Science, vol. 9, No. 3, 1950, pp. 323-347.

Edwards, Merrill, Burton, Alan C., "Correlation of Heat Output and Blood Flow in the Finger, Especially in Cold-Induced Vasodilation," Journal of Applied Physiology, vol. 15, 1960, pp. 201-208.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Finkelstein, Stanley M., Cohn, Jay N., "First- and Third-Order Models for Determining Arterial Compliance," Journal of Hypertension, vol. 10, supplement 6, Aug. 1992, pp. 511-514.

Millasseau, Sandrine C, Guigui, Franck G, Kelly, Ronan P., Prasad, Krishna, Cockcroft, John R., Ritter, James M., Chowienczyk, Philip

(56) References Cited

OTHER PUBLICATIONS

J., "Noninvasive Assessment of the Digital Volume Pulse: Comparison with the Peripheral Pressure Pulse," Hypertension, vol. 36, No. 6, Dec. 2000, pp. 952-956.

Fitchett, D., Bouthier, Jd, Simon, A. CH., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

\* cited by examiner

CONTINUOUS NON-INVASIVE BLOOD PRESSURE MEASUREMENT APPARATUS AND METHODS PROVIDING AUTOMATIC RECALIBRATION

CROSS REFERENCE TO RELATED APPLICATIONS

This application is a continuation of U.S. patent application Ser. No. 12/275,453, filed on Nov. 21, 2008, which is a continuation of U.S. patent application Ser. No. 11/015,033, filed Dec. 20, 2004, now U.S. Pat. No. 7,455,643, which is a continuation-in-part of U.S. patent application Ser. No. 10/884,962, filed Jul. 7, 2004, now abandoned, which claims priority to U.S. Provisional Application No. 60/484,640, filed Jul. 7, 2003, all of which are incorporated by reference herein in their entireties.

FIELD OF THE INVENTION

This invention relates to apparatus for continuous non-invasive blood pressure (CNIBP) measurement.

BACKGROUND

There are various devices for measuring the blood pressure of subjects in a continuous and non-invasive manner. Some such devices exploit the fact that the pulse transit time (or speed of propagation of heart pulse waves, or pulse wave velocity) varies with blood pressure (and a number of other factors). If all other factors are equal then one can track changes in blood pressure by monitoring the pulse transit time or the speed at which pressure pulses propagate. One device which exploits this principle is described in U.S. Pat. No. 6,599,251 entitled CONTINUOUS NON-INVASIVE BLOOD PRESSURE MONITORING METHOD AND APPARATUS, which is hereby incorporated herein by reference. This device determines blood pressure based on a differential pulse transit time (DPTT) which is measured between two pulse waveforms obtained from two pulse signal detectors, for example optical pulse oximetry sensors, at two peripheral sites on a subject. DPTT is inversely proportional to the pulse propagation speed or pulse wave velocity. An increasing DPTT reflects a decreasing pulse propagation speed and an increasing blood pressure, and vice versa.

One issue with such CNIBP devices is that there are a large number of interacting factors which can effect the pulse propagation speed (or pulse wave velocity) or DPTT. These factors include:

the effects of vasoactive drug administration which alters the compliance of the arteries,
changes in the subject's physical position,
changes of sensor locations,
changes in the subject's blood density, and so on.

Because the condition of a subject can vary over time the relationship between blood pressure and pulse propagation speed (or pulse wave velocity) or DPTT can also vary over time. It is therefore necessary to recalibrate blood pressure measurement systems which rely on pulse propagation speed (or pulse wave velocity) or DPTT measurements. Recalibration involves taking one or more reference blood pressure measurements. Reference blood pressure measurements may be obtained by way of any suitable alternative blood pressure measurement system such as a cuff-based system, an oscillometric blood pressure measurement mechanism, or the like. The reference blood pressure measurements can be used to redetermine coefficients in a CNIBP calculation formula which, for example, relates DPTT to blood pressure.

It is difficult to predict when the cumulative effect of factors which can affect the calculation that relates blood pressure to DPTT or pulse wave velocity of a CNIBP system is sufficient to require that the system be recalibrated. This is especially true in the environments in which such systems are often used. There is no simple rule for when to manually recalibrate a CNIBP system which takes into account all the effects that may lead to changes to the relationship between blood pressure and the pulse propagation speed (or pulse wave velocity) or DPTT. There is, therefore, a need for systems capable of reliably triggering recalibration when necessary.

SUMMARY OF THE INVENTION

This invention provides CNIBP methods and apparatus which automatically determine when it is necessary to perform a recalibration. The methods and apparatus monitor features of pulse waves in a subject and initiate recalibration when the monitored features differ from corresponding reference features in a stored template.

A first aspect of the invention provides a method for maintaining calibration of a continuous non-invasive blood pressure (CNIBP) measurement system. The method comprises performing a calibration by: obtaining for a subject a reference blood pressure value, reference CNIBP data (e.g. DPTT or pulse wave velocity) at the point reference blood pressure is taken and reference pulse wave data; calculating and storing coefficients of a CNIBP calculation formula based on the reference blood pressure value and the reference CNIBP data; and, storing a template comprising information characterizing one or more characteristics of the reference pulse wave data. The reference pulse wave data corresponds to one or more reference pulse waves and is used for determining when recalibration should be triggered. Subsequently, the method obtains subsequent pulse wave data characterizing one or more subsequent pulse waves of the subject and evaluates a recalibration condition comparing the subsequent pulse wave data to the template. If the subsequent pulse wave data and template satisfy the recalibration condition, the method repeats performing the calibration of the CNIBP measurement system.

Another aspect of the invention provides apparatus for continuous non-invasive blood pressure (CNIBP) measurement. The apparatus comprises: a reference blood pressure measurement mechanism; at least one CNIBP sensor having an output signal which varies with a blood pressure of a subject; and a CNIBP controller. The CNIBP controller is configured to compute a blood pressure of the subject from the output signal according to a CNIBP calculation formula comprising at least one coefficient. The CNIBP controller is configured to trigger the reference blood pressure measurement mechanism to obtain a reference blood pressure and to use the reference blood pressure to determine a new value for the at least one coefficient by: monitoring a pulse wave signal representing pulse waves of the subject; valuating a recalibration condition comparing pulse waves in the pulse wave signal to a stored template; and, determining whether the pulse waves and template satisfy the recalibration condition.

Further aspects of the invention and features of various embodiments of the invention are set out below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
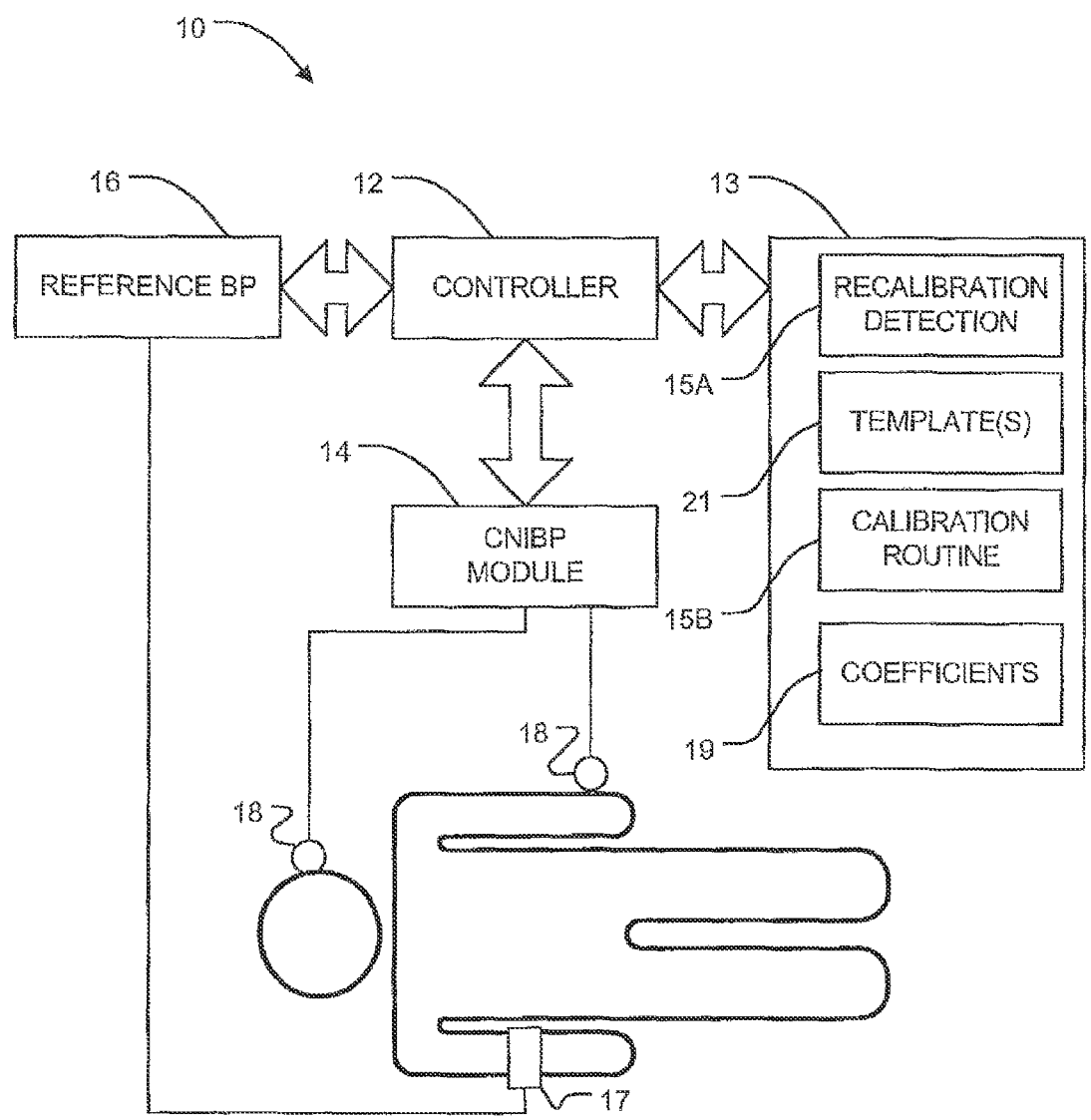
FIG. 1 is a block diagram of a CNIBP measurement system.

FIG. 1 shows a CNIBP measurement system 10 according to the invention. System 10 includes a CNIBP controller 12 which controls the operation of CNIBP measurement system 10. CNIBP controller 12 also controls the operation of a reference blood pressure measurement module 16. CNIBP controller 12 has access to a data store 13. Data store 13 may comprise a combination of storage devices accessible to CNIBP controller 12 and may include registers and other embedded memory in a processor or other devices within CNIBP controller 12. CNIBP controller 12 executes computer software instructions of recalibration detection software 15A. Under the control of software 15A, CNIBP controller 12 monitors a number of parameters and determines from the monitored parameters whether it is appropriate to trigger a recalibration of system 10.

If CNIBP controller 12 determines that it is appropriate to recalibrate system 10 then CNIBP controller 12 triggers the operation of a calibration routine 15B. Under the control of calibration routine 15B, CNIBP controller 12 causes reference blood pressure measurement module 16 to obtain a reference measurement of the subject's blood pressure. Based upon the reference measurement, CNIBP controller 12 determines new coefficients 19 for a blood pressure calculation formula. CNIBP controller 12 stores the new coefficients in data store 13.

In the illustrated embodiment, reference blood pressure measurement module 16 includes a blood pressure detecting means 17 which may include one or more sensors. Blood pressure detecting means 17 comprises any suitable detector for obtaining a reliable measurement of blood pressure. For example, blood pressure detecting means 17 may comprise: a cuff-based system, an oscillometric blood pressure measurement mechanism, or the like. Various blood pressure measurement systems suitable for use as blood pressure detecting means 17 are known.

Under control of calibration routine 15B, CNIBP controller 12 uses a reference blood pressure based upon a signal from blood pressure detecting means 17 to calibrate CNIBP measurement system 10. Calibration involves determining new coefficients for a CNIBP calculation formula that presents the relationship between blood pressure and pulse propagation speed (or pulse wave velocity) or DPTT. Subsequently, CNIBP measurement system 10 operates using the new coefficients to provide measurements of the subject's blood pressure until the next time recalibration detection software 15A determines that it is necessary to recalibrate system 10.

In an example embodiment of the invention, system 10 receives a signal from a sensor which detects pulse waves in a subject. In the illustrated embodiment of the invention, system 10 includes at least two sensors 18 which detect pulse waves on the subject. In the illustrated embodiment, pulse waves are detected by the same sensors 18 which also provide inputs for CNIBP measurement system 10. The illustrated system 10 detects a pulse wave at each of sensors 18 and determines blood pressure, at least in part, from a difference in the times at which the pulse wave arrives at sensors 18.

Figure 2:
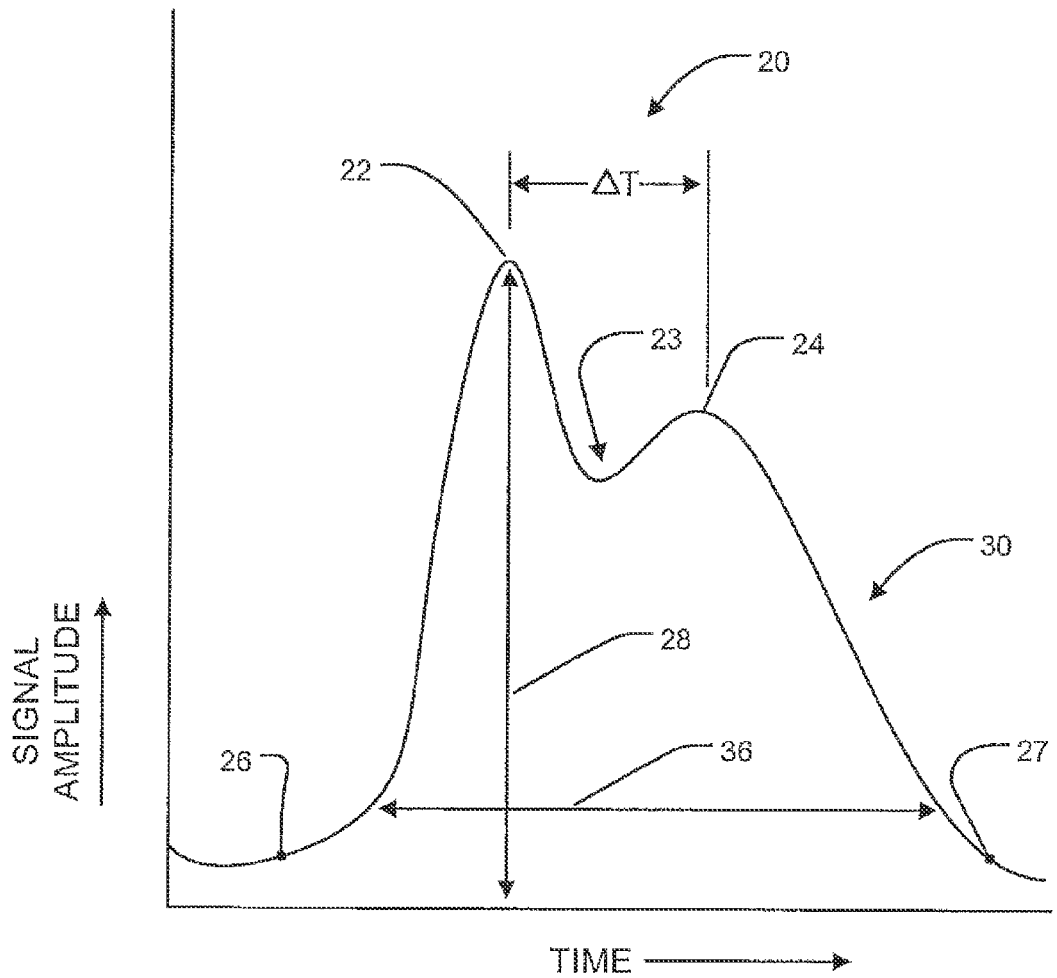
FIG. 2 is a plot of a pulse signal.

CNIBP controller 12 monitors a number of features of the pulse waves. FIG. 2 is an example of a pulse wave signal 20 as might be detected by a pulse-oximetry-type sensor associated with CNIBP measurement system 10. Pulse wave 20 has a systolic peak 22, a dichrotic notch 23 and a reflected wave peak 24. Pulse wave signal 20 may be digitized. In the illustrated embodiment, a CNIBP module 14 includes appropriate signal processing electronics and analog to digital converter(s) (not shown) to acquire and digitize signals from sensors 18 and to make the digitized signals available to CNIBP controller 12. Those skilled in the art are familiar with the design and construction of circuits for the acquisition and digitization of signals from sensors such as pulse-oximetry-type sensors.

Figure 3:
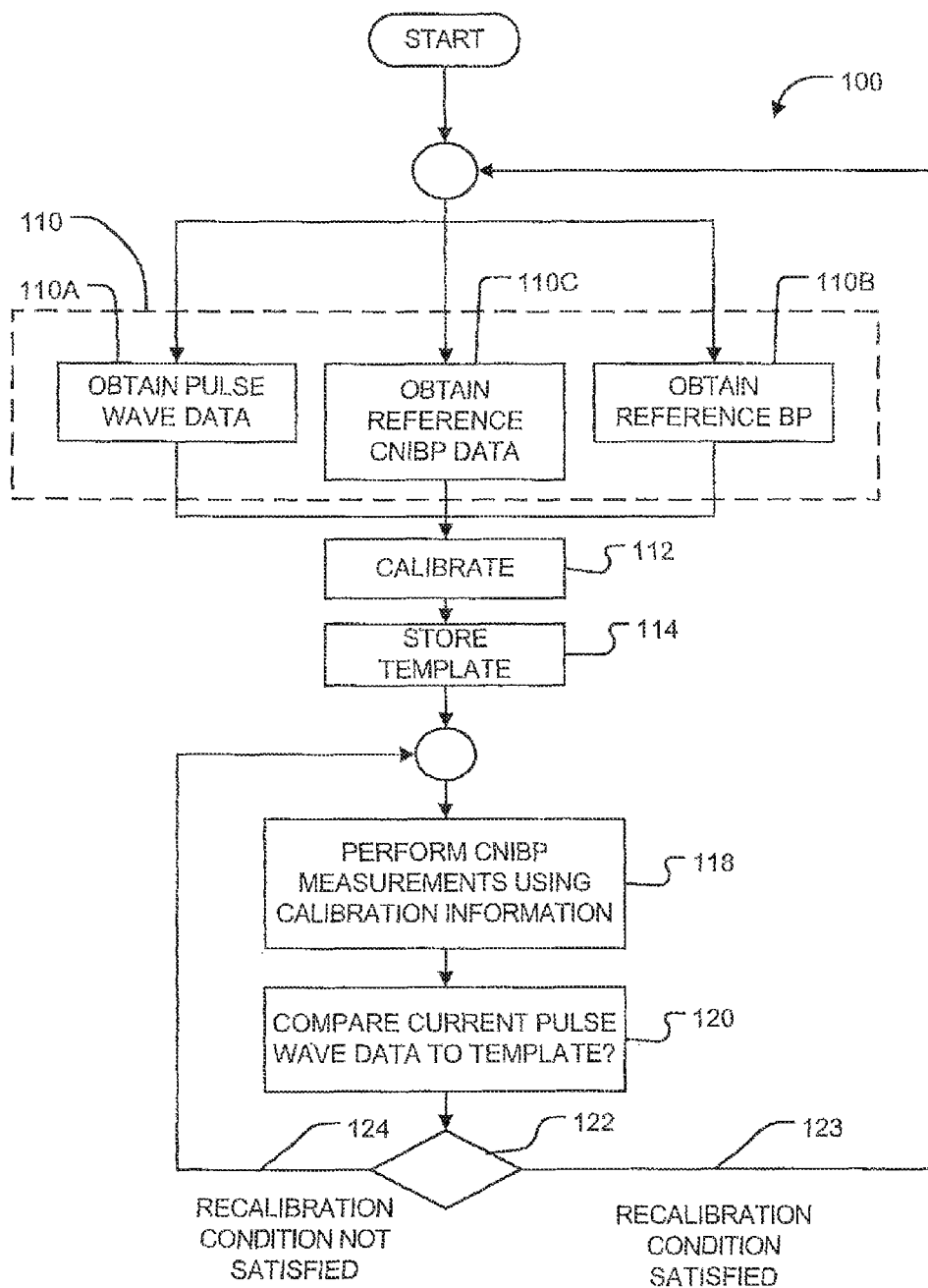
FIG. 3 is a flow chart illustrating a method according to the invention.

Pulse wave 20 has a number of features. These features are illustrated in FIG. 3. One feature of pulse wave 20 is its area.

A second feature of pulse wave 20 is the height of systolic peak, or "pulse amplitude", 22. In FIG. 2 the pulse amplitude is indicated by arrow 28.

A third feature of pulse wave 20 is the shape of pulse wave 20. The shape of the portion 30 of pulse wave 20 is believed to be especially sensitive to at least some factors that can make recalibration necessary in its portion 30 between systolic peak 22 and end point 27.

A fourth feature is the time differences, $\Delta T$, between systolic peak 22 and reflected wave peak 24 and/or between systolic peak 22 and dichrotic notch 23.

In one embodiment of the invention CNBIP measurement system 10 is calibrated in an initial calibration. During the initial calibration, each of the above features, the pulse wave area, the pulse height, the time, $\Delta T$ between the systolic peak 22 and reflected wave peak 24 or dichrotic notch 23, and the shape of portion 30 of pulse wave 20 are each characterized. Information characterizing these features is stored as a collection of parameters in data store 13. The stored collection of these parameters may be called a template 21 (see FIG. 1).

Periodically, for example on each heartbeat, or after each group of several heartbeats, or at spaced apart times, each of the parameters is determined for a current pulse wave, or a current group of pulse waves, and the result is compared to a stored template 21. Typically stored template 21 is a template stored at a time of the most recent calibration. If the difference between the measured parameters and the parameters of the stored template 21 exceeds a threshold according to a suitable metric then a recalibration is triggered.

Various metrics may be used to quantify the difference between a set of parameters measured at a particular time and the corresponding parameters of a stored template 21. In simple cases, each of the parameters is compared to its counterpart in the stored template 21. In the alternative, particular combinations of the parameters, or information derived from the parameters, may be compared to one another.

The stored template 21 may constitute raw stored measured parameter values, stored pulse wave data from which those parameter values can be determined, or the result of one or more calculations based upon the measured parameter values.

The shape of part 30 of waveform 20 may be recorded, for example, by storing a number of points from portion 30 of the waveform in a data store. When a subsequent measurement is made of the shape of portion 30 of a subsequent pulse wave, the difference can be computed, for example, as:

an average of the absolute values of differences between corresponding ones of the points on the two pulse waves;

an average of the sum of squares of differences between corresponding ones of the points of the two pulse waves;

the result of another correlation calculation between a subsequent measurement and the stored template 21;

fitting a fitting function to each of the two pulse waves and comparing coefficients of the fitted fitting function;

some combination of these; or the like.

The area of pulse wave 20 may be determined by integrating pulse wave 20 between a chosen start point 26, and a suitably chosen end point 27. The end point may, for example, be at the consequent diastolic valley. The start point may, for example, be at the foot of the pulse wave or the diastolic valley.

Instead of integrating the area of a pulse wave 20, CNIBP controller 12 could measure the height and width of a pulse wave 20 as indicated by arrows 28 and 36 in FIG. 2. The product of height and width measurements could be used in place of the area parameter. If this is done, the measurement indicated by arrow 36 should be taken at a signal amplitude which is smaller than the amplitude of dichrotic notch 23. The amplitude at which width 36 is measured may be a function of the amplitude at one or more points in wave form 20, such as a function of amplitudes at systolic peak 22 and/or reflected wave peak 24. A reference value for pulse wave area may be compared directly to a current value of pulse wave area, for example by subtraction or division.

The time difference ΔT may be determined in any of various suitable ways including:

performing peak detection on raw pulse wave data to identify the systolic peak 22 and reflected wave peak 24 and/or dichrotic notch 23 and to determine how far apart they are in time;

using cross-correlation methods to locate the peaks and/or the notch;

computing a first derivative of pulse wave 20 to find systolic and diastolic peaks 22, 24 and/or either one of the peaks and notch 23;

computing a second derivative of pulse wave 20 to find to find systolic and diastolic peaks 22, 24 and/or either one of the peaks and notch 23;

some combination of these techniques, etc.

A reference value of ΔT may be compared directly to a current value of ΔT, for example by comparing the result of a subtraction or division of the reference and current values of ΔT to a threshold.

If the relationship between the reference parameters of the template and the current parameters satisfies a recalibration condition then CNIBP controller 12 initiates a recalibration routine. The recalibration condition may include comparing a current value of one or more of the above parameters to a corresponding value from a stored template. The condition may be the logical "OR" of two or more sub-conditions. The sub-conditions may include, for example, two or more of:

the difference in the area parameter exceeds a first threshold;

the difference in the ΔT parameter exceeds a second threshold;

the difference in the shape parameter exceeds a third threshold;

an average or weighted average of differences in two or more of the area, ΔT and shape parameters exceeds a fourth threshold;

and so on.

The sub-conditions could also include one or more additional sub-conditions such as:

more than a specified time has passed since the most recent recalibration;

the calculated value for the subject's blood pressure differs from the most-recently-obtained reference blood pressure by more than a threshold amount (for example ±30%);

an average rate of change of the subject's calculated blood pressure has exceeded a threshold amount over a predetermined period;

some combination of these sub-conditions etc.

Optionally system 10 includes a first mechanism for triggering recalibration based upon features of pulse wave 20 and a second mechanism for triggering recalibration on the basis of time since the last recalibration.

FIG. 3 illustrates a method 100 according to the invention. In block 110, method 100 acquires pulse wave data (block 110A) for later use in determining whether recalibration is necessary, a reference blood pressure value (block 110B) and reference CNIBP data (block 110C) for determining CNIBP calculation coefficients in calibration. In block 112, the reference blood pressure and the pulse wave or DPTT data are used to derive calibration information for CNIBP measurement system 10. The calibration information may comprise, for example, one or more parameters which affect the CNIBP calculation of the subject's blood pressure.

In block 114 a template 21 is stored. The template is based upon the pulse wave information obtained in block 110A. Block 114 may be performed at any time after the pulse wave information has been obtained. Block 114 may be performed prior to, after or simultaneously with the calibration performed in block 112. The data stored in block 114 may be combined values (e.g. combined by averaging) describing characteristics of one or more pulse waves taken during the calibration process.

In block 118 CNIBP measurements are performed using the calibration information determined in block 112. The CNIBP measurements are periodically updated. The CNIBP data may be obtained, for example, each time a single or multiple heartbeats are detected at sensors 18 (see FIG. 1).

In block 120, current pulse wave data is obtained, processed if necessary, and compared to the template which was stored in block 114. Block 122 determines whether or not a recalibration condition, which is based upon the pulse wave data and the stored template 21, is satisfied. If block 122 determines that the recalibration condition is satisfied then method 100 loops back to perform another calibration on path 123. If block 122 discovers that the recalibration condition is not satisfied then method 100 loops back to continue performing CNIBP measurements on path 124.

In some embodiments of the invention, the recalibration condition and/or one or more sub-conditions of the recalibration condition include a parameter that affects the sensitivity of the condition or sub-condition. Whether or not the condition or sub-condition is satisfied depends upon the current value of the sensitivity parameter, the value(s) used as inputs for the condition or sub-condition and any threshold(s) used in evaluating the condition or sub-condition. For example, where a sub-condition compares a number derived from a feature of a waveform to a threshold, the sensitivity parameter may comprise a factor that adds to, subtracts from, multiplies or divides the threshold and/or the derived number being compared to the threshold. The value of the sensitivity factor affects what values for the derived number will cause the condition or sub-condition to be satisfied.

Separate sensitivity parameters may be provided for each of a plurality of sub-conditions. Apparatus according to the invention may provide an interface which permits a user to vary one or more sensitivity parameters. A single user input may simultaneously control values of multiple sensitivity parameters.

In some cases, motion artifacts could cause system 10 to measure values that result in a recalibration condition to being satisfied in a case where the condition would not be satisfied in the absence of the motion artifact.

System 10 may comprise an artifact detecting mechanism, that monitors the signals received from sensors 18 for characteristics which tend to indicate the presence of motion artifacts. For example some motion artifacts include components much higher and/or much lower frequencies than heartbeat frequencies. Some motion artifacts have characteristic waveforms. Motion artifacts can result in rapid fluctuations in DPTT. The artifact detecting mechanism could include one or more of:

A mechanism that detects high and/or low frequency components in the pulse wave signal(s). For example, software or hardware that performs a time-to-frequency domain transformation such as a fast Fourier transform on one or more of the signals being monitored;

A mechanism that attempts to match a waveform of one or more of the signals being monitored to patterns characteristic of motion artifacts. For example, software or hardware that performs pattern matching; and, A mechanism that detects rapid variations in measured DPTT. For example, the mechanism may detect whether DPTT varies by more than a threshold amount, for example ±20%, between adjacent pulses.

The artifact detecting mechanism may comprise a software routine and/or suitable hardware. The artifact detecting mechanism may trigger a timer upon an artifact being detected.

In some embodiments of the invention the artifact detection mechanism suppresses recalibration being triggered or, in the alternative suppresses recalibration being triggered by one or more selected sub-conditions, for a predetermined time after an artifact is detected. In some embodiments system 10 is configured to trigger recalibration, even if recalibration would not otherwise be triggered, in cases where artifacts are detected over a significant period. For example, upon detection of a motion artifact, system 10 may suppress recalibration for a first time period, for example a period in the range of 5-45 seconds, typically about 30 seconds. If artifacts continue to be detected so that recalibration is still being suppressed at the end of a second, longer, time period, for example a time period in the range of 45 seconds to 1 or 2 minutes, then system 10 may trigger a recalibration.

In some instances the artifact detection mechanism may detect a motion artifact while a calibration is being performed. Systems according to some embodiments of the invention are configured to ignore results of the calibration being performed in response to the detection of a motion artifact. Such systems may terminate the acquisition of a blood pressure by reference blood pressure measurement module 16 in response to the detection of a motion artifact. In response to detection of the motion artifact, the system may suppress recalibration for a short period, as described above, and/or schedule the interrupted calibration to be performed after a suitable interval which is long enough for effects of the motion artifact to have subsided and is also long enough to permit blood pressure measurement module 16 to be reset, if necessary.

Certain implementations of the invention comprise computer processors which execute software instructions which cause the processors to perform a method of the invention. For example, one or more processors in a CNIBP controller may implement the methods of FIG. 3 by executing software instructions in a program memory accessible to the processors. The invention may also be provided in the form of a program product. The program product may comprise any medium which carries a set of computer-readable signals comprising instructions which, when executed by a computer processor, cause the processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, RAM, flash RAM, or the like, or transmission-type media such as digital or analog communication links. The instructions may optionally be stored on the medium in a compressed and/or encrypted format.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

in some embodiments of the invention, a template may be stored for each of a number of different prior calibration events. Measured parameters may be compared to each of the stored templates to find a stored template which is closest to the measured parameters. A calibration associated with that closest template may be used. In such embodiments of the invention recalibration may be triggered only if the measured parameters are sufficiently different from all of the stored templates. The stored templates may each expire and be deleted after a given time.

The templates are not necessarily based upon data for a single pulse wave. Templates may be constructed from data from several pulse waves which may be combined by averaging or the like.

The recalibration condition need not be based on data from a single pulse wave but may involve comparing data derived from two or more pulse waves to a template.

In some embodiments of the invention a recalibration system generates a signal which indicates that recalibration should be initiated manually rather than automatically performing the recalibration.

The invention may be embodied in a module which generates a signal which may be used to trigger recalibration of a separate CNIBP system.

Accordingly, the scope of the invention is to be construed in accordance with the substance defined by the following claims.

What is claimed is:

1. A method for operating a blood pressure measurement system, comprising:
   activating a blood pressure detector to obtain a first blood pressure measurement of a subject;
   detecting, by a pulse oximetry sensor, a pulse wave signal from the subject comprising a plurality of individual pulses;
   determining, using a processor, a reference parameter of the pulse wave signal proximate the time of the first blood pressure measurement;
   storing, using the processor, the reference parameter as a template;
   determining, using the processor, a morphology metric of one or more individual pulses of the pulse wave signal, wherein the morphology metric comprises one of an area of the one or more individual pulses, an amplitude of the one or more individual pulses, a shape of the one or more individual pulses, and a time difference of the one or more individual pulses;
   quantifying, using the processor, a difference between the morphology metric and the template; and
   triggering the blood pressure detector to obtain a second blood pressure measurement of the subject when the difference passes a threshold.

2. The method of claim 1, further comprising tracking, using the processor, a time duration since the first blood pressure measurement, and triggering the blood pressure detector to obtain the second blood pressure measurement when the difference passes a threshold or when the time duration exceeds a limit.

3. The method of claim 1, wherein the morphology metric is determined from a current group of individual pulses.

4. The method of claim 1, further comprising calculating, using the processor, a continuous blood pressure measurement after the first blood pressure measurement and before the second blood pressure measurement.

5. The method of claim 4, wherein calculating the continuous blood pressure measurement comprises calculating blood pressure from a differential pulse transit time.

6. The method of claim 5, further comprising re-calibrating, using the processor, the continuous blood pressure measurement by adjusting the calculation of the differential pulse transit time, based on the morphology metric of the pulse wave signal.

7. The method of claim 1, further comprising adjusting, using the processor, the threshold or the difference based on a sensitivity factor.

8. The method of claim 1, further comprising periodically updating, using the processor, the template.

9. The method of claim 1, wherein the template comprises a reference pulse wave.

10. A method for operating a blood pressure measurement system, comprising:
    activating a blood pressure detector to obtain a first blood pressure measurement of a subject;
    detecting, by a pulse oximetry sensor, a pulsatile signal from the subject, the pulsatile signal comprising a plurality of pulses;
    determining, using a processor, first and second reference parameters of the pulsatile signal proximate the time of the first blood pressure measurement;
    determining, using the processor, first and second morphology parameters of the plurality of pulses, wherein each of the first and second morphology metric parameters comprises one of: an area of the one or more individual pulses, an amplitude of the one or more individual pulses, a shape of the one or more individual pulses, and a time difference of the one or more individual pulses;
    comparing, using the processor, the first morphology parameter to the first reference parameter, and the second morphology parameter to the second reference parameter;
    evaluating, using the processor, a new measurement condition based on the comparisons; and
    when the new measurement condition is satisfied, triggering the blood pressure detector to obtain a second blood pressure measurement of the subject.

11. The method of claim 10, wherein evaluating the new measurement condition comprises performing a logical OR operation of the first and second comparisons.

12. The method of claim 10, further comprising determining, using the processor, a time duration since the first blood pressure measurement, and satisfying the new measurement condition when the time duration passes a limit.

13. The method of claim 10, further comprising calculating, using the processor, a continuous blood pressure measurement after the first blood pressure measurement, based at least in part on the pulsatile signal.

14. The method of claim 10, further comprising applying, using the processor, a sensitivity factor to one or more of the comparisons.

15. The method of claim 10, further comprising monitoring, using the processor, the pulsatile signal for an indication of motion, and wherein evaluating the new measurement condition comprises finding the new measurement condition to be unsatisfied when the indication of motion is present.

16. The method of claim 10, wherein comparing the first and second morphology parameters to the first and second reference parameters, respectively, comprises quantifying a difference between the first morphology parameter and the first reference parameter and quantifying a difference between the second morphology parameter and the second reference parameter.

17. A method for operating a blood pressure measurement system, comprising:
    detecting, using a pulse oximetry sensor, a pulse wave signal of a subject;
    monitoring, using a processor, a morphology characteristic of the pulse wave signal over time, wherein the morphology characteristic comprises one of an area of a pulse, an amplitude of a pulse, a shape of a portion of a pulse, and a time difference between first and second portions of a pulse;
    storing, using the processor, a reference characteristic of the pulse wave signal;
    comparing, using the processor, the monitored characteristic to the reference characteristic;
    evaluating, using the processor, a new measurement condition based on the comparison; and
    triggering a blood pressure detector to obtain a blood pressure measurement when the new measurement condition is satisfied.

* * * * *